United States Patent
Zal

(10) Patent No.: US 10,988,730 B2
(45) Date of Patent: Apr. 27, 2021

(54) SAND WORM LYOPHILISATE AND USES THEREOF

(71) Applicant: HEMARINA, Morlaix (FR)

(72) Inventor: Franck Zal, Ploujean-Morlaix (FR)

(73) Assignee: Hemarina, Morlaix (FR)

( * ) Notice: Subject to any disclaimer, the term of this patent is extended or adjusted under 35 U.S.C. 154(b) by 230 days.

(21) Appl. No.: 14/889,041

(22) PCT Filed: May 14, 2014

(86) PCT No.: PCT/FR2014/051118
§ 371 (c)(1),
(2) Date: Nov. 4, 2015

(87) PCT Pub. No.: WO2014/184492
PCT Pub. Date: Nov. 20, 2014

(65) Prior Publication Data
US 2016/0152944 A1    Jun. 2, 2016

(30) Foreign Application Priority Data

May 16, 2013    (FR) .................................... 13 54399

(51) Int. Cl.
| | | |
|---|---|---|
| *C12N 1/38* | (2006.01) | |
| *A23K 20/147* | (2016.01) | |
| *A23K 50/40* | (2016.01) | |
| *A23K 50/80* | (2016.01) | |
| *A23K 10/20* | (2016.01) | |
| *A23J 1/04* | (2006.01) | |
| *A23K 1/10* | (2006.01) | |
| *A23K 1/18* | (2006.01) | |

(52) U.S. Cl.
CPC .................. *C12N 1/38* (2013.01); *A23J 1/04* (2013.01); *A23K 1/10* (2013.01); *A23K 1/188* (2013.01); *A23K 1/1846* (2013.01); *A23K 10/20* (2016.05); *A23K 20/147* (2016.05); *A23K 50/40* (2016.05); *A23K 50/80* (2016.05)

(58) Field of Classification Search
None
See application file for complete search history.

(56) References Cited

U.S. PATENT DOCUMENTS

| | | | | |
|---|---|---|---|---|
| 2003/0181358 | A1* | 9/2003 | Zal | .................. C07K 14/43536 435/69.1 |
| 2005/0032196 | A1* | 2/2005 | Duwat | ..................... C12N 1/04 435/252.9 |
| 2008/0057156 | A1* | 3/2008 | Geppel | .................. A23C 9/123 426/15 |
| 2012/0040453 | A1* | 2/2012 | Zal | ......................... C12M 23/24 435/325 |

FOREIGN PATENT DOCUMENTS

| | | |
|---|---|---|
| WO | 2005/037392 A2 | 4/2005 |
| WO | 2006/016135 A2 | 2/2006 |

OTHER PUBLICATIONS

Duwat, P., et al. 2001 Journal of Bacteriology 183(15): 4509-4516. (Year: 2001).*
"Grand view of the kingdom of life" (2014).

* cited by examiner

*Primary Examiner* — Marsha Tsay
(74) *Attorney, Agent, or Firm* — W&C IP

(57) ABSTRACT

The invention relates to a lyophilisate or to a powder including i) at least one globin, a globin protomer or an extracellular hemoglobin from annelids, and ii) at least one biological material from annelids that is different from said globin, from said protomer and from said hemoglobin.

6 Claims, No Drawings

SAND WORM LYOPHILISATE AND USES THEREOF

The present invention relates to a lyophilisate or a powder comprising i) at least one extracellular hemoglobin, globin or globin protomer from annelids, and ii) at least one biological material from annelids that is different from said globin, said protomer and said hemoglobin.

The growth of microorganisms on the industrial scale is a major preoccupation of the technologies which exploits these microorganisms. Indeed, in order to produce food (yogurts, beers, wines), but also medicaments (penicillin, etc.) or biofuels (ethanol, biogas), numerous microorganisms of different nature and having different properties are used. Bioreactor culture requires the relevant microorganism strain(s), the substrate, and also the culture conditions to be selected.

Hemin is often used as a bioreactor culture additive. This product is a protoporphyrin IX, or a chemical or natural analog, which contains iron and is complexed with chlorine. It comes from mammals, in particular from cattle or pigs, or else is synthesized by chemical processes, and is in particular used in an industrial fermentation bioreactor.

However, this product is very difficult to dissolve and to stabilize, and is thereby not suitable for a bioreactor culture. Moreover, this product can be dangerous, in particular due to the presence of viruses, bacteria, yeasts or prions, potentially transmissible or pathogenic to humans, and is absolutely not suitable for the production of kosher and/or halal products by microorganisms.

There is therefore a need for a product which is compatible with bioreactor culture, which is not derived from mammals, and which is pathogen-free.

The applicant has discovered, surprisingly, that the use of a lyophilisate or of a powder, obtained from whole annelids, or from annelid coproducts (i.e. remaining worm products obtained following extraction of the annelid hemoglobin), or else from lyophilized annelid hemoglobin, makes it possible to obtain a good fermentation yield, in particular lactic fermentation yield, while providing iron. This molecule does not precipitate from the culture medium of the bioreactor, and therefore makes it possible to maintain good homogeneity. This lyophilisate also has advantageous nutritional properties, which make it compatible with its integration into food products, in particular animal feed products.

The applicant has now found that the use of whole annelids or of annelid coproducts, which have been milled and lyophilized, makes it possible to obtain a good fermentation yield, in particular lactic fermentation yield, while providing iron. These whole annelids or these annelid coproducts, which have been milled and lyophilized, also constitute an advantageous source of animal feed.

The invention therefore relates to a lyophilisate or a powder comprising i) at least one extracellular hemoglobin, globin or globin protomer from annelids, and ii) at least one biological material from annelids different that said globin, from said protomer and from said hemoglobin.

Preferably, the lyophilisate or the powder is obtained from whole annelids or from annelid coproducts, which have been milled beforehand. Such a lyophilisate is intended to be used as a lactic fermentation improver.

As indicated above, the term "annelid coproduct" is intended to mean the worm fraction remaining after the extraction of the hemoglobin from said annelid.

The lyophilisate or the powder according to the invention therefore comprises, firstly, i) at least one extracellular hemoglobin, globin or globin protomer from annelids. The extracellular hemoglobin from annelids is present in the three classes of annelids: the polychaetes, the oligochaetes and the achaetes. Reference is made to extracellular hemoglobin because it is not naturally contained in a cell, and can therefore circulate freely in the bloodstream without chemical modification to stabilize it or to make it functional. The extracellular hemoglobin from annelids is a giant biopolymer with a molecular weight of between 2000 and 4000 kDa, consisting of approximately 200 polypeptide chains of between 4 and 12 different types which are generally grouped into two categories.

The first category, with 144 to 192 components, groups together the "functional" polypeptide chains which bear an active site of heme type, and are capable of reversibly binding oxygen; these are chains of globin type, the weights of which are between 15 and 18 kDa and which are very similar to the $\alpha$- and $\beta$-type chains of vertebrates.

The second category, with 36 to 42 components, groups together the "structural" or "linker" polypeptide chains which have few or no active sites but enable the assembly of the subunits called one-twelfth subunits or protomers.

Each hemoglobin molecule consists of two superposed hexagons which have been named hexagonal bilayer, and each hexagon is itself formed by the assembly of six subunits (or "one-twelfth subunits" or "protomers") in the shape of a drop of water. The native molecule is made up of twelve of these subunits (dodecamer or protomer). Each subunit has a molecular weight of between 200 and 250 kDa, and constitutes the functional unit of the native molecule. According to the invention, the lyophilisate may also comprise at least one globin protomer of the extracellular hemoglobin from annelids. Said protomer constitutes the functional unit of the native hemoglobin, as indicated above.

Finally, the lyophilisate may also comprise at least one globin chain of the extracellular hemoglobin from annelids. Such a globin chain may in particular be chosen from the Ax and/or Bx type globin chains of extracellular hemoglobin from annelids.

The extracellular hemoglobin from annelids, globin protomers thereof and/or globins thereof may be native or recombinant.

Preferably, the extracellular hemoglobin, globin or protomer from annelids is chosen from the extracellular hemoglobins from polychaete annelids, preferably from the extracellular hemoglobins from the family Arenicolidae and the extracellular hemoglobins from the family Nereididae. Even more preferentially, the annelids are chosen from *Arenicola* sp and *Nereis* sp, and even more preferentially *Arenicola marina* or *Nereis virens*.

The lyophilisate or the powder according to the invention also comprises ii) at least one biological material from annelids different from said globin, from said protomer and from said hemoglobin.

The expression "biological material different from said globin, said protomer and said hemoglobin" is intended to mean any biological material (cells, tissues or organs) which is different than the extracellular hemoglobin, than the protomer and than the globin. This biological material also comes from annelids, it being possible for said annelids to be identical to or different than the annelid from which the hemoglobin, the globin or the protomer i) is extracted. Preferably, said biological material ii) is an annelid coproduct.

A subject of the present invention is also a process for preparing the lyophilisate, obtained from whole annelid worms or from annelid coproducts. This process in fact comprises:
  i) the freezing of whole annelids or of annelid coproducts at a temperature of between −20° C. and −100° C. for a time of at least 24 h;
  ii) the sublimation of the frozen product obtained in i) for at least 2 h, under vacuum;
  iii) the final drying of the sublimated product obtained in ii), until a dry product is obtained; and
  iv) the milling of the dry product obtained in iii).

The lyophilization cycle comprises three steps:
freezing (step i) of the process according to the invention):

This first phase consists in freezing the solution in such a way that the water contained is converted into ice.

Preferably, the freezing in step i) of the process according to the invention is carried out at a temperature of between −20° C. and −90° C. for at least 24 h, preferably at least 48 h. Preferably, the freezing is carried out at approximately −80° C. for at least 24 h, preferably at least 48 h;

primary desiccation or sublimation (step ii) of the process according to the invention):

The sublimation step allows the ice present in the frozen solution to go from the solid state to the gas state, without an intermediate step. The frozen solution is dried out by the application of a vacuum; the ice then becomes vapor.

The sublimation is carried out using a high-vacuum pump, a mechanical pump or a cryopump. Preferably, the sublimation in step ii) is carried out for at least 4 h;

secondary desiccation or final drying (step iii) of the process according to the invention):

When the ice is totally sublimated, the secondary desiccation phase can begin. It makes it possible to extract, by desorption, the water molecules trapped at the surface of the dried products.

At the end of step iii), the lyophilisate obtained comprises between 1% and 5% by weight of water.

The milling in step iii) can for example be carried out using a mortar, a helical mill or a ball mill in order to obtain a fine powder.

The powder according to the invention can also be obtained by any means which enables a dry powder to be obtained.

The lyophilisate or the powder can be stored in glass or plastic, preferably glass, bottles or vials. The lyophilisate or the powder can be used as they are or placed in solution.

The lyophilisate or the powder according to the invention is easy to transport and to store, it can thus be easily reconstituted, and is ready to be used.

The present invention also relates to a solution comprising the lyophilisate or the powder according to the invention. Such a solution can be obtained by simply mixing the lyophilisate or the powder with a diluent. The lyophilisate or the powder can in fact be diluted at the appropriate moment with the diluent, in order to restore the initial milled material. Preferably, the diluent is ultrapure water. Alternatively, preferably, the diluent is an aqueous solution comprising sodium chloride, calcium chloride, magnesium chloride, potassium chloride, and also sodium gluconate and sodium acetate, and has a pH of between 6.5 and 7.8, preferably equal to 7.1±0.5, preferably of approximately 7.35. Said solution preferably has an osmolarity of between 300 and 350, and preferentially of 302 mOsmol/l.

More preferentially, the diluent is chosen from ultrapure water and an aqueous solution comprising 90 mM of NaCl, 23 mM of Na-gluconate, 2.5 mM of $CaCl_2$, 27 mM of Na-acetate, 1.5 mM of $MgCl_2$, and 5 mM of KCl, and a pH of 7.1±0.5, which can contain between 0 and 100 mM of antioxidant of ascorbic acid and/or reduced gluthatione type.

It is also possible to dilute the lyophilisate or the powder in a solution of sodium hydroxide (NaOH), in particular in a solution of sodium hydroxide of 0.01 to 1 N. The dilution of the powder or of the lyophilisate according to the invention in a solution of sodium hydroxide makes it possible, on the one hand, to increase the solubility of the lyophilisate or of the powder, but also to potentially depyrogenate it (i.e. destroy the endotoxins). The dissolving time depends on the concentration of sodium hydroxide used. It generally ranges from 24 hours for low concentrations of sodium hydroxide, up to one hour for high concentrations.

A subject of the invention is also the use of a lyophilisate or of a powder according to the invention, or of a solution comprising the same, or of a lyophilized or powdered hemoglobin from annelids, for improving bioproduction. The term "bioproduction" is intended to mean the production of a biological product on an industrial scale, preferably in a bioreactor. The term "biological product" is intended to mean in particular a protein (i.e. amino acid sequence comprising at least 50 amino acids. Preferably, the protein is an antibody, a hemoglobin or an enzyme), a peptide (i.e. amino acid sequence comprising from 2 to 49 amino acids), a nucleic sequence or a plasmid. Indeed the lyophilisate or the powder according to the invention, or the solution which comprises same, and also the hemoglobin, can be used in bioreactors to increase the bioproduction yield. In addition, the lyophilisate or the powder according to the invention, or the solution which comprises the same, and also the hemoglobin, can be added to the culture media of animal or plant cells, for example CHO cells. They make it possible in particular to improve the growth of said cells.

A subject of the invention is also the use of a lyophilisate or of a powder according to the invention, or of a solution comprising the same, or else of a lyophilized or powdered hemoglobin from annelids, for improving the yield of lactic fermentation. Lactic fermentation is carried out by lactic acid bacteria, typically in a bioreactor. It does not require oxygen (anaerobic), and consists of the conversion of glucose into lactic acid. As demonstrated in the example, the lyophilisate according to the invention, once reconstituted, has good stability and good functionality; it comprises in particular extracellular hemoglobin.

A subject of the invention is also the use of a lyophilisate or of a powder according to the invention, or of a solution comprising same, or else of a lyophilized or powdered hemoglobin from annelids, as an animal feed, in particular for aquatic animals and pets.

This feed can be in the form of bait, granules, paste, pellets or powder.

It is particularly suitable as whole feed or as feed additive for fish, or for invertebrates such as molluscs, crustaceans, cephalopods, corals, or else for pets.

The invention is now illustrated by the following examples, which are in no way limiting.

EXAMPLE 1: PREPARATION AND ASSAYING OF LYOPHILISATES ACCORDING TO THE INVENTION

Materials & Methods

Worm Powders

The products tested are powders of *Arenicola marina* and of *Nereis virens*.

These powders were obtained by lyophilization and milling.

The following media were tested:

MEDIUM 1: milliQ $H_2O$

MEDIUM 2: Extraction buffer (400 mM NaCl, 2.95 mM KCl, 32 mM $MgSO_4 \cdot 7H_2O$, 11 mM $CaCl_2$, 50 mM Tris base, 10 mM ascorbic acid)

MEDIUM 3: 1N NaOH (used to redisperse the Hemin, hemoglobin of bovine origin).

Method 1 g of powder was weighed into a 15 ml centrifuge tube. 3 ml of solution were added and then homogenized, firstly manually and then with a vortex. Photographs were taken of this mixture. This mixture was then centrifuged at 5000 g for 10 minutes. The pellet and the supernatant were then photographed. The supernatant was recovered and frozen at −80° C. Given the small volumes recovered, the experiment was repeated, but on 3 g of powder and 9 ml of solution in 50 ml centrifuge tubes. Aliquots were frozen at −80° C.

For the analytical tests, fresh material was generated in greater amount 3 g of worm powder were weighed out and then resuspended in 15 ml of the redispersion solution. The material was then centrifuged and the supernatant was recovered and then filtered through 0.8 μm and 0.22 μm filters. The functionality and the purity were determined and an assay was carried out on the samples.

Results

1. Lyophilization

For 5 kg of *Arenicola,* 670 g of powder were generated, i.e. a factor of 7.5.

For 6 kg of *Nereis,* 921 g of powder were generated, i.e. a factor of 6.5.

2. Analytical Results a) Assay

The hemoglobin concentrations are between 3 and 8 g/kg of fresh worms.

|  | Arenicola | | | Nereis | | |
| --- | --- | --- | --- | --- | --- | --- |
|  | Water | Tris buffer | Extraction buffer | Water | Tris buffer | Extraction buffer |
| [M101] in g/l with a ⅓ dilution | 8 | 8 | 11 | 4 | 7 | 9 |
| [M101] in g/kg of worm powder | 38 | 40 | 56 | 22 | 36 | 47 |
| [M101] in g/kg of fresh worms | 5 | 5 | 8 | 3 | 6 | 7 | b) Conductivity

The conductivity of the solids is high (~130 mS/cm).

EXAMPLE 2: TESTS WITH THE LYOPHILISATES ACCORDING TO THE INVENTION

Materials & Methods

Worm Powders
HEMARINA A: from *Arenicola marina*
HEMARINA B: from *Nereis virens*
The powders were obtained as in example 1.
Sample Preparation
i) Flask culture: dissolution of the powders at 200 g/l then filtration of the supernatant and addition to the flasks.
ii) Bioreactor culture: direct addition to the reactors in a proportion of 1 g/l of powder before autoclaving.
Culture Conditions
i) Flask (100 ml, 0.5 and 1 l) culture:
The strain used is a strain of *Lactococcus lactis* SB50.
The tests were carried out overnight (16-18 h) at 30° C. with shaking at 180 rpm.
The composition of the culture medium for the strain is the following: glucose (1%), maltose (0.1%), yeast extract (2%) and minerals.
The culture conditions are the following: filling to 10% useful volume; a positive control with addition of hemin (hemoglobin of bovine origin) at 10 ppm final concentration is used.
The HEMARINA samples (powders in solution) were added post-sterilization after centrifugation.
ii) Bioreactor (1 l useful volume) culture:
The tests were carried out overnight (15-16 h) at 30° C.
The composition of the culture medium for the strain is identical to that of the flasks, with an addition of 0.01% antifoam.
The culture conditions are the following: filling to 60% useful volume, $pO_2$ regulated at 20% or 80% and pH regulated at 6.
1 g/l of powder are added directly to the culture medium before autoclaving.
The optical density (OD) at 600 nm is measured for each culture.

Results i) Flask Culture:

The ODs are the following:

| Reference | OD at 600 nm |
|---|---|
| Control (Lc lactis alone) | 1.52 |
| Positive control (Lc lactis + hemin 10 ppm) | 4.5 |

The active concentration of each product (HEMARINA A and HEMARINA B) is equivalent to that of hemin, i.e. is approximately 0.25 ppm.

ii) Bioreactor Culture:

The results are the following:

|  | Control | Positive control | HEMARINA A |
|---|---|---|---|
| OD at 600 nm | 10.63 | 10.9 | 12.07 |
| Dry weight (g/l) | 2.8 | 3.4 | 4.1 |
| Volume $NH_4OH$ (ml) | 18.2 | 12.3 | 15.8 |
| Viability (CFU/ml) | 1.75E+09 | 5.03E+09 | 6.42E+09 |

The viability of the strain is improved three- to four-fold in the presence of the HEMARINA A or HEMARINA B products.

The production of lactic acid (corresponding to the volume of $NH_4OH$ produced) is less than the control but more than the positive control (hemin).

The acidifying capacity of the HEMARINA A and HEMARINA B products is equivalent to that of the positive control.

In conclusion, it appears that the HEMARINA A and HEMARINA B products make it possible to improve the viability of lactic acid strains, and have a very good acidifying capacity.

These products could replace bovine and porcine hemins, which are widely used in the food-processing fields, but which have potential risks of viral or prion contamination in humans, and which are not suitable for the production of kosher and/or halal products.

The invention claimed is:

1. A method for improving the yield of fermentation carried out by microorganisms, comprising providing to the microorganisms in a culture medium, a pathogen-free lyophilisate or a powder obtained from whole annelids which have been milled beforehand, wherein the pathogen-free lyophilisate or powder comprises i) at least one extracellular hemoglobin, globin or globin protomer from annelids, wherein said hemoglobin, globin or globin protomer comprises iron, and ii) at least one biological material from annelids that is different from said globin, from said protomer and from said hemoglobin, wherein the annelid is chosen from the Arenicolidae family or the Nereididae family and wherein the pathogen-free lyophilisate or powder is provided in an amount sufficient to improve the yield of fermentation carried out by the microorganisms, and wherein the microorganisms are lactic acid bacteria and the fermentation is lactic acid fermentation.

2. The method of claim 1, wherein the at least one biological material from annelids that is different from said globin, from said protomer and from said hemoglobin is an annelid coproduct.

3. The method of claim 2, wherein the annelid coproduct is a worm fraction remaining after extraction of hemoglobin from the annelid.

4. The method of claim 1, wherein the culture medium comprises at least sugar, yeast extract and minerals.

5. The method of claim 1, wherein the microorganisms are in a bioreactor.

6. A method for improving the yield of fermentation carried out by microorganisms, consisting essentially of providing to the microorganisms, in a culture medium, a pathogen-free lyophilisate or a powder obtained from whole annelids which have been milled beforehand, wherein the pathogen-free lyophilisate or powder comprises i) at least one extracellular hemoglobin, globin or globin protomer from annelids, wherein said hemoglobin, globin or globin protomer comprises iron, and ii) at least one biological material from annelids that is different from said globin, from said protomer and from said hemoglobin, wherein the annelid is chosen from the Arenicolidae family or the Nereididae family and wherein the pathogen-free lyophilisate or powder is provided in an amount sufficient to improve the yield of fermentation carried out by the microorganisms, and wherein the microorganisms are lactic acid bacteria and the fermentation is lactic acid fermentation.

* * * * *